US005788657A

United States Patent [19]

Burns

[11] Patent Number: 5,788,657
[45] Date of Patent: Aug. 4, 1998

[54] PAIN RELIEVING PRESSURE DEVICE

[76] Inventor: Donald S. Burns, 26211 Via Oceano, Mission Viejo, Calif. 92692

[21] Appl. No.: 862,165
[22] Filed: May 22, 1997
[51] Int. Cl.$^6$ ........................................ A61H 7/00
[52] U.S. Cl. .................................. 601/134; D24/215
[58] Field of Search ........................ 601/18, 20, 21, 601/80, 81, 154, 135; 607/1, 3, 115, 145, 149, 150, 151; D24/200, 214, 215

[56] References Cited

U.S. PATENT DOCUMENTS

| 202,094 | 4/1878 | Clarke. | |
|---|---|---|---|
| 279,524 | 6/1883 | Beaty. | |
| 489,832 | 1/1893 | Reud. | |
| 564,258 | 7/1896 | Rossbach. | |
| 1,000,294 | 8/1911 | Rosenberg. | |
| 2,100,234 | 11/1937 | Belknap | 128/24.5 |
| 4,262,672 | 4/1981 | Kief | 128/329 |
| 4,653,473 | 3/1987 | Kempe | 128/1 R |
| 5,385,530 | 1/1995 | Wu | 601/21 |

*Primary Examiner*—William E. Kamm
*Attorney, Agent, or Firm*—Gene Scott-Patent Law & Venture Group

[57] ABSTRACT

A small hand-held device having a body of electrically insulating material, and a central rod of electrically conductive material provides for the rod extending beyond a proximal and a distal ends of the body to form electrical contacts. Therefore an electrical conduction path is set-up between the contacts. This path is advantageously used to establish a charge state on the skin surface so as to help in relieving localized pain. A pointed proximal end of the device enables an effective massaging action when the device is brought into contact with the skin and pressed into it.

4 Claims, 2 Drawing Sheets

FIG. 1
FIG. 2
FIG. 3
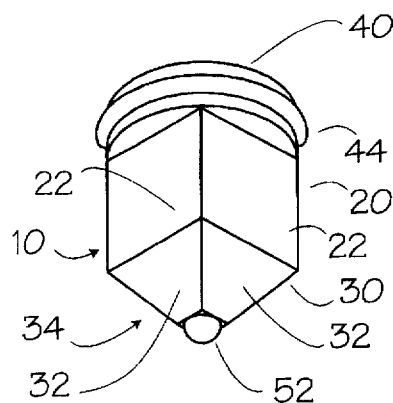
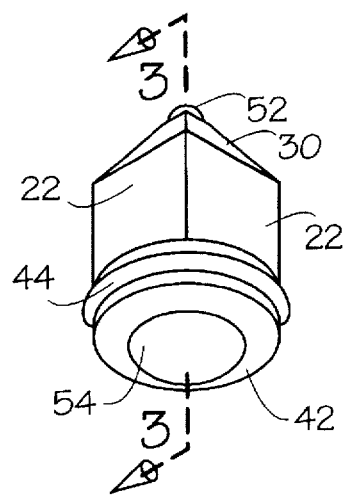
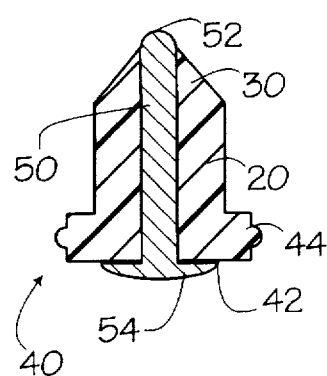
FIG. 4
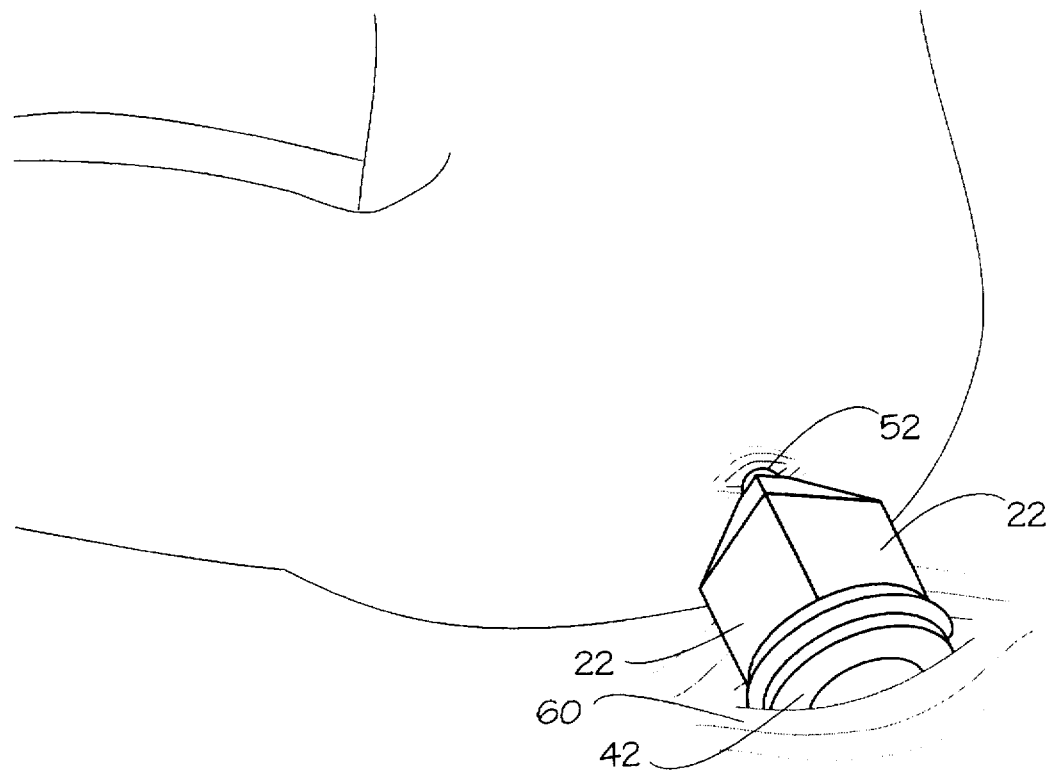

PAIN RELIEVING PRESSURE DEVICE

BACKGROUND OF THE INVENTION

1. Field of the Invention:

This invention relates generally to devices for relieving minor pains and aches, and more particularly to a hand-held device for relieving pain through the use of soothing pressure and massage in an area of the flesh where pain is concentrated, and also by changing the local electromagnetic field in the painful area.

2. Description of Related Art

The following art defines the present state of this field:

Clarke, U.S. Pat. No. 202,094 describes an improvement in canes. This invention uses a combination of a galvanic battery with a cane, in such a manner that the use of the cane induces a gentle current of the fluid through the palm of the hand. A gentle electric current directed through the peculiarly nervous structure of the palm of the hand is capable of producing an important influence for good.

Beaty, U.S. Pat. No. 279,524 describes a thimble composed of two or more layers of material adapted to generate an electric current; the exterior of said thimble being provided with indentations or corrugations.

Reud, U.S. Pat. No. 489,832 describes an invention that relates to that class of electric batteries which are adapted to be worn upon or applied to the body of a person, so as to send a mild current through certain diseased parts to strengthen, stimulate and cure them. This invention will generate a strong electric current in proportion to its size, which is made active by contact with acids or liquids of the body. It is also of such shape and construction that it may be conveniently and easily inserted in and removed from any of the body apertures, to the end that it may be used internally as well as externally.

Rossbach, U.S. Pat. No. 564,258 describes an electric massage apparatus. The object of the invention is a massaging device, which can be operated with or without electrodes, and which acts in both cases automatically.

Rosenberg, U.S. Pat. No. 1,000,294 describes an electromagnetic vibrator for local application to the person. This invention relates to an improved instrument for the production and local application to the person, of continues, rapid, and intense mechanical vibration. Oscillations of a character suited to the treatment of various maladies, which are capable of being temporarily or permanently amelcation thereto of the mechanical vibratory massage.

Belknap, U.S. Pat. No. 2,100,234 describes a massaging device. The device will include a battery or coil casing of the general shape of a flashlight casing, the same having one side thereof the massaging tool whereby the device will be portable and may be easily manipulated during treatment of the parts to be massaged.

Kief, U.S. Pat. No. 4,262,672 describes an acupuncture instrument for use in producing analgesia that comprises of a needle having a head and an electrical connection for applying a transformer arrangement. This includes an electric coil constituting a secondary winding of the transformer arrangement and having two poles, one of the poles being insulated therefrom. The electric coil being arranged on the needle head and being capable of being surrounded by another coil constituting a primary winding of the transformer arrangement. An annular electrode electrically connected to the other pole of the secondary winding and insulated with respect thereto and vertically movably arranged on the secondary winding.

Kempe, U.S. Pat. No. 4,653,473 describes a method of reducing pain resulting from exposed or damaged nerve ends, such as the pain in amputees commonly referred to as phantom limb pain. The method may also reduce pain resulting from arthritis. This method involves covering the affected area with a radiation-shielding textile, whether by fashioning a garment from the textile or using a sheet or cover. The radiation-shielding textile found to be suitable is a cloth woven of yarn consisting of a textile fiber, such as nylon, and from two to thirty-five percent by weight of conductive metal filament.

Wu, U.S. Pat. No. 5,385,530 describes a massaging apparatus employing a voltage-producing device. The voltage-producing device produces an instantaneous impulse voltage for passing a current to the veins, arteries and vital points of a human body to stimulate the function of the internal organs.

The prior art teaches body massage apparatus of various types as shown above. However, the prior art does not teach that such a device may be advantageously shaped to provide the advantages of the present invention. The present invention provides advantages as described in the following summary.

SUMMARY OF THE INVENTION

The present invention teaches certain benefits in construction and use which give rise to the objectives described below.

The present invention provides a small hand-held device having a body of electrically insulating material, and a central rod of electrically conductive material. The rod extends beyond a proximal and a distal ends of the body to form electrical contacts and an electrical conduction path between them.

A primary objective of the present invention is to provide a hand-held pain reducing massage apparatus having advantages not taught by the prior art.

Another objective is to provide such an apparatus with physical features that enable the device to be used with the soft surface of a mattress, for instance, to prop the device for hands-free use.

A further objective is to provide such an apparatus with physical features that enable the device to be pressed into the flesh for deep massage action.

A further objective is to provide such an apparatus with physical features that enable the device to provide a common surface electrical charge between the skin over a painful area of the human body and a palm of a hand.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 1 is a perspective view of the preferred embodiment of the device of the present invention showing the distal end of the device;

FIG. 2 is a perspective view of the preferred embodiment of the device of the present invention showing the proximal end of the device;

FIG. 3 is a section view thereof taken along line 3-3 of FIG. 2 showing further details of an electrically conducting element of the invention;

FIG. 4 is a perspective view thereof showing one manner of using the invention for hip pain.

DETAILED DESCRIPTION OF THE INVENTION

Figure 5:
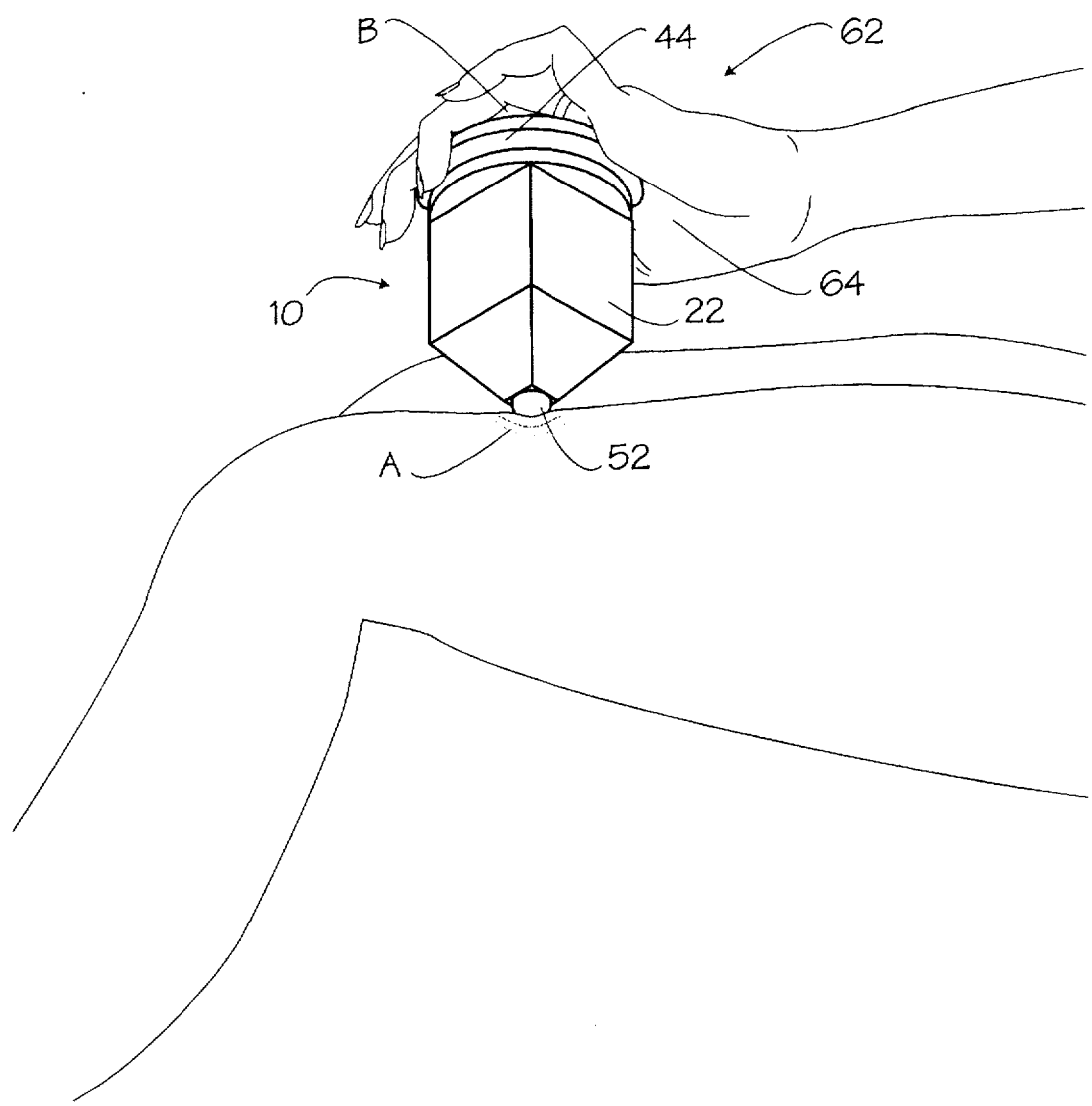
FIG. 5 is a perspective view thereof showing one manner of using the invention for leg pain.

The above described drawing figures illustrate the invention, a pain relieving device comprising a body 10 of an electrically insulating rigid material such as wood or plastic. The body 10 includes a multi-sided central body portion 20 integral with a convergent distal end portion 30 and an opposing, mushrooming, proximal handle portion 40 having a flattened plateaued terminus 42. Preferably, the central body portion 20 provides four planar sides 22. The handle portion 40 is preferably palm sized with a circular peripheral edge 44. The convergent distal end portion 30 is preferably pyramidal shaped having sloping planar sides 32.

An electrically conductive central rod 50, made of a copper, silver or preferably, gold, forms a rounded distal contact 52, preferably ¼ to ⅜ inches in diameter, at a distal end 34 of the distal end portion 30 and a flattened proximal contact 54 on the terminus 42 of the proximal handle portion 40, the central rod 50, distal contact 52, and proximal contact 54 being integrally formed as an equi-potential body.

The device, as shown in FIGS. 4 and 5, is preferably small and light enough so as to be manipulated into contact with various parts of the human body when pain occurs. The central body portion 20 is multi-sided so that sides 22 as well as the flattened plateaued terminus 42, may be rested against bed clothing 60, for instance, as shown in FIG. 4. The ability to rest the device for self support is important to gain the advantage of hands-off use. Such sides 22 enable the device to rest with a degree of stability so that the device will not easily roll when one shifts ones weight or moves slightly.

The distal end portion 30 is convergent and preferably pyramidal in shape so as to enable the device to be pushed into the flesh to a certain degree without meeting excessive resistance. As the distal contact 52 is pressed against the flesh, it pushes the flesh inwardly, the surrounding flesh surface forms a natural cavity into which the distal end portion 30 conveniently fits. As described above and shown in FIG. 4, the device is advantageously placed on a soft and resilient surface, such as the surface of a mattress, with the relatively large surface area of the flattened plateaued terminus 42, resting in contact with the resilient surface and the distal contact 52 pressed against the flesh. In this manner the device is prevented from unduly sinking into the resilient surface, so that an appropriate degree of pressure may be applied to that portion of the human body in contact with the rounded distal contact 52.

The handle portion 40 is comfortably held in one hand 62 with the palm 64 of the hand touching the proximal contact 54. The circular peripheral edge 44 enables the handle portion 40 to fit the hand 62 comfortably. With the distal contact 52 in contact with the skin at, let us say, point "A" on the body, a portion of the body experiencing pain, and with the proximal contact 54 in contact with point "B", the skin surface of one hand, the electrical surface charge state of point "A" and point "B" become equal. That is, charge is exchanged between points "A" and "B" along central rod 50 until the same charge state exists at both points. This occurs because the material of central rod 50 and the proximal and distal contacts 52, 54, being good electrical conductors, cannot support an electric field so that the charge state throughout the central rod 50 and its terminal contacts 52, 54, and any surface touching the contacts 52, 54 is common. Also, assuming that the skin has some moisture on its surface, a good electrical contact is made between contacts 52, 54 and the skin, so that the charge condition on the skin surface at these points is the same as that of the central rod 50. The relationship between pain generation and propagation in the human body, and the static charge state on the skin is not fully understood at this time, but it is found that when the skin surface adjacent to a point of pain is brought into contact with a good conductor, especially when the conductor is contacted by another, remote, portion of the skin's surface, this act has the tendency to reduce the level of pain or to eliminate it completely after a few minutes. When such contact is supplemented by minor massage and movement of the conductor on the skin surface, the result is improved. One theory advanced relative to the cause and effect relationship established in the operation of the present invention advances the notion that a weak electromagnetic field exists within the skin and underlying body flesh. This field is comprised of the Earth's magnetic field and the net electric field associated with the many polar molecules within the flesh. The very localized electric fields of polar molecules within the flesh tend to neutralize each other so that no net field may exist. However, over small areas of flesh there can be a weak field established due to the alignment of polar molecules and due to surface electric charge. It is well understood that the small size of the distal contact 52 makes it a focus for electric field lines. Therefore surface and subsurface charge carriers, on and within the skin, are advantageously effected by the presence of this aligned field either toward the contact 52, or away from it. The resultant reduction in pain may be simply due to a narcotic effect the change in charge state or the movement of charge has on the neuron pain transmitters near the massage site, rather than any actual lessening of the causes of the pain themselves, but this is not known.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A pain relieving device comprising:
   a body of an electrically insulating rigid material, the body including:
      a multi-sided central body portion integral with
      a convergent distal end portion and
      an opposing, mushrooming, proximal handle portion having a flattened plateaued terminus;
   an electrically conductive central rod forming a rounded distal contact at a distal end of the distal end portion and a flattened proximal contact on the terminus of the proximal handle portion, the central rod, distal contact and proximal contact being integrally formed as an equi-potential body.

2. The device of claim 1 wherein the central body portion provides four planar sides.

3. The device of claim 1 wherein the handle portion is palm sized with a circular peripheral edge enabling the hand to close around the handle portion while remaining in contact with the proximal contact.

4. The device of claim 1 wherein the convergent distal end portion is pyramidal in shape and the distal contact is ¼ to ⅜ inches in diameter.

* * * * *